United States Patent
Pizzi Spadoni

(10) Patent No.: US 6,526,983 B1
(45) Date of Patent: Mar. 4, 2003

(54) RIGID SHELL SPLINT

(75) Inventor: Luigi Pizzi Spadoni, Camrore (IT)

(73) Assignee: Spencer Italia SRL (IT)

( * ) Notice: Subject to any disclaimer, the term of this patent is extended or adjusted under 35 U.S.C. 154(b) by 0 days.

(21) Appl. No.: 10/049,892
(22) PCT Filed: Jun. 21, 2000
(86) PCT No.: PCT/IT00/00255
§ 371 (c)(1), (2), (4) Date: Feb. 13, 2002
(87) PCT Pub. No.: WO01/13827
PCT Pub. Date: Mar. 1, 2001

(30) Foreign Application Priority Data

Aug. 20, 1999 (IT) .................... PR990014 U

(51) Int. Cl.⁷ .................................. A61F 5/37
(52) U.S. Cl. .......................... 128/870; 5/624
(58) Field of Search ................. 128/846, 845, 128/869, 870; 5/624, 625, 628

(56) References Cited

U.S. PATENT DOCUMENTS 5,113,876 A * 5/1992 Herman ............ 128/870
6,055,988 A * 5/2000 Perisho ............ 5/628

* cited by examiner

Primary Examiner—Michael A. Brown
Assistant Examiner—S Green
(74) Attorney, Agent, or Firm—Shlesinger, Fitzsimmons & Shlesinger

(57) ABSTRACT

The present invention pertains to the field of rigid shell extricators for immobilizing and transporting traumatized persons. An extricator (1) bears one or more niches (6) and (6a) obtained in the thickness of the extricator itself in correspondence with the occipital area and of the torso of the traumatized person. Each of said niches is provided with a lid, respectively (8) and (8a). Inside the niches (6) and (6a) are stowed the holding belts which can be extracted through openings (12) present peripherally in the thickness of said extricator.

4 Claims, 2 Drawing Sheets

RIGID SHELL SPLINT

TECHNICAL FIELD AND BACKGROUND ART

The present invention relates to a rigid shell extricator.

When rescuing trauma victims, and particularly victims of road accidents, the need arises to prevent lesions secondary to the traumas and due to posture and rescue, transportation, and diagnosing stresses.

The immobilisation of trauma victims is one of the very few and simple interventions which, if effected in a timely and proper manner, can determine the destiny of the persons involved and set the time and social costs of their hospitalisation and recovery.

The occipital area and the pelvis, together with the entire development of the spine, are the anatomical parts that most need an effective immobilisation, obtained by laying the traumatised body onto specifically studied and constructed supports, which have long been in use; such supports are aptly called extricators.

Extricators are based on the principle of immobilising the articulated masses of the spine to a rigid body in order to eliminate elastic dissipation in the inter-vertebral articulations and, consequently, to reduce to nil the energy applied on any lesion points.

The rigidity of the extricators involves at least their longitudinal development, correspondingly to the longitudinal development of the trauma victim's spine.

In other words, by immobilising the traumatised person one obtains a substantial uniformity of reaction of that person's entire body to the stresses deriving from the most disparate sources of motion which may be encountered during the rescue operations.

The immobilization also prevents the traumatized person, due to loss of lucidity, from involuntarily making movements which might further damage his/her health. The extractors, which may be variedly shaped, can substantially be sub-divided in two types: those including a single, fully rigid, bed, and called shell extricators, or those presenting a structure provided with vertical rigidity and horizontal flexibility and including a plurality of rigid elements set mutually side-by-side and parallel.

All extricator models currently in use present the drawback that the belts with which they are provided are fastened only at an extremity to the related extricator, letting the other one dangle freely; this fact presents the real possibility not only of constituting a hindrance to the motion of the extricator, but also the more serious possibility of constituting a hazard: consider the eventuality of tripping in the freely dangling belts.

In some models of extricators, the attempt to overcome this dangerous drawback was made by providing the aforementioned belts with quick fastening mechanisms and the related extricator with attachments rationally conceived for the actual rapid fastening of said belts.

Such a solution provides for the belts to be normally detached from the related extricator and to be fastened thereon only at the time the equipment is actually used.

It is obvious that such a solution solves only partially the problem of the belts being free to dangle, since the fact that they are separate from the extricator may lead to their loss or, in any case, their unavailability for immediate use just when, due to the seriousness of certain situations, the utmost rapidity of intervention is necessary.

Another drawback present by many of the extricators currently used is that they are not constructed according to the most recent knowledge acquired through bio-mechanical research studies.

From U.S. Pat. No. 4,945,583 a device for transporting disabled or sick persons it is known comprising a stretcher mattress attachable to a stretcher frame or a transport vehicle.

The stretcher frame comprises a plurality of belt take-up mechanisms for attaching the stretcher mattress to the frame.

The mattress has belts merging into a third belt inside the mattress for connecting to the stretcher frame.

The mattress has also a housing for a take-up device located in a recess of the mattress. Other take-up devices are associated to the frame.

Notwithstanding the presence of many take-up devices, said document clearly discloses that the belts are freely pending out of the mattress and only a part of them can be housed inside the mattress: a portion of the belt must remain outside the mattress or outside the frame to let the operator to pull out the belt.

DISCLOSURE OF INVENTION.

The aim of the present invention is to eliminate the aforesaid drawbacks and to make available a rigid extricator provided with holding belts that are completely inserted thereinto and can easily and rapidly be extracted therefrom.

In particular, a rigid shell extricator, of the type with rigid platform, constituting the subject of the present invention is characterised in that one or more niches are obtained in the thickness of the aforesaid extricator; said niches have their open side obtained on a lower surface of the extricator opposite to an upper surface thereof, destined to support a traumatised person; the niches are positioned in correspondence with the points of the extricator destined to support the occipital area and torso of a traumatised person; the niches are provided with lids.

BEST MODE FOR CARRYING OUT THE INVENTION

This and other features shall become more readily apparent in the description that follows of a preferred embodiment illustrated, purely by way of non limiting example, in the accompanying drawing tables, in which.

Figure 1:
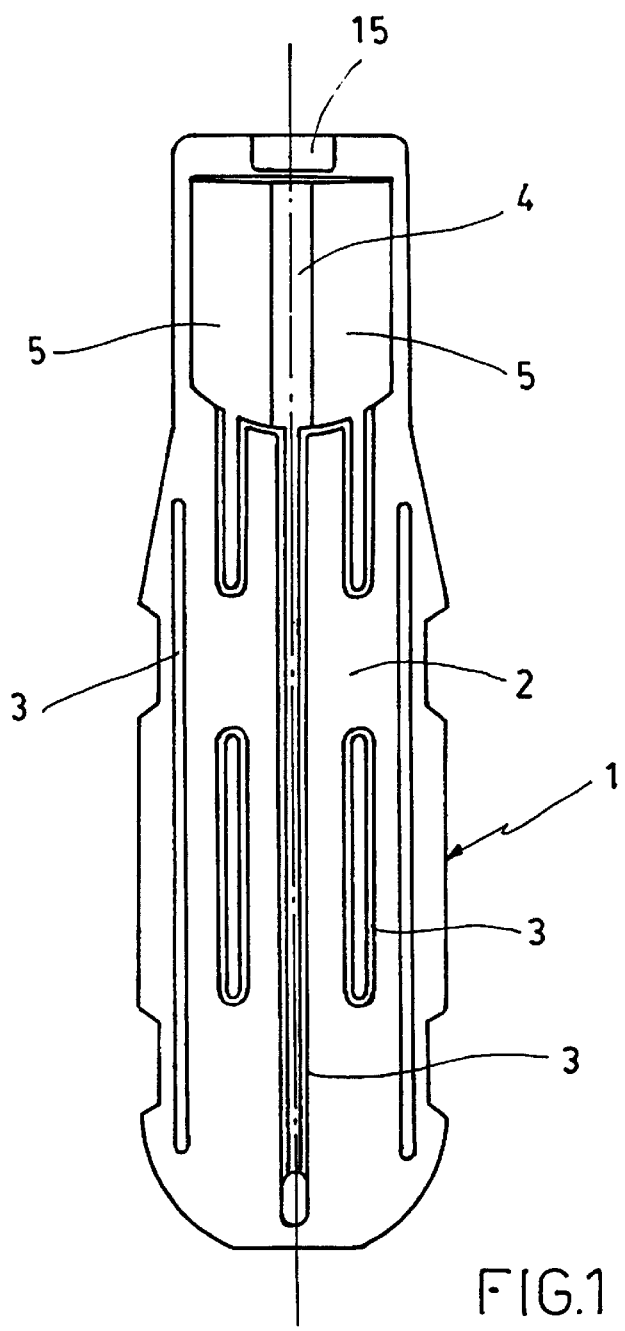
FIG. 1 shows a plan view of the extricator on the side supporting the trauma victim.
Figure 2:
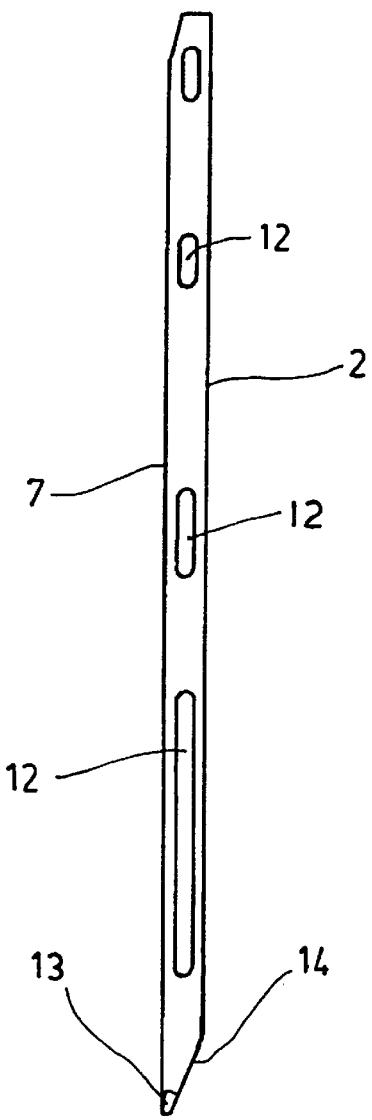
FIG. 2 shows a side view of the extricator.
Figure 3:
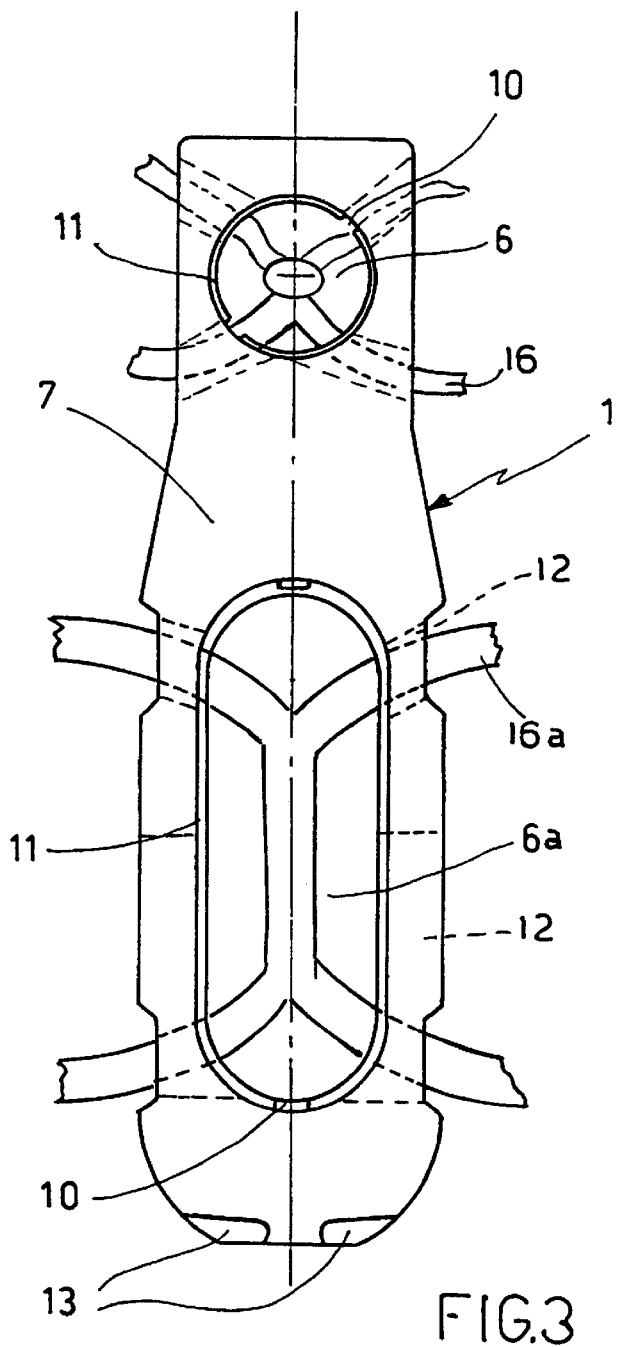
FIG. 3 shows the item illustrated in FIG. 1 but from the opposite side.
Figure 4:
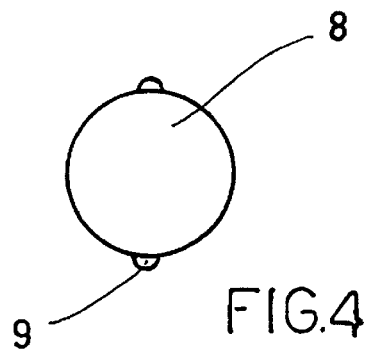
FIG. 4 shows a front view of the lid positioned in correspondence with the occipital area.
Figure 5:
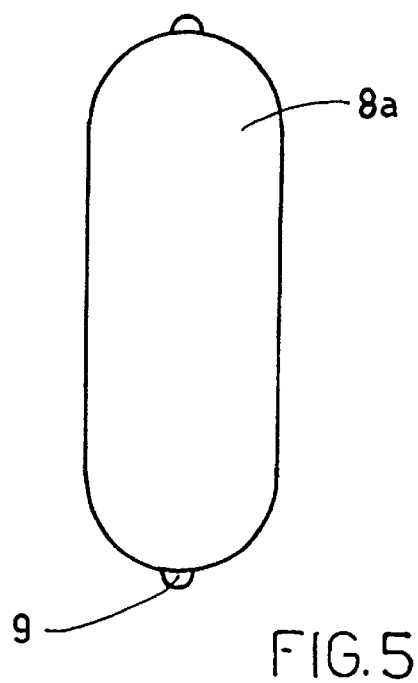
FIG. 5 shows a front view of the lid positioned in correspondence with the torso area.

With reference to the figures, the number 1 indicates a shell extricator of the kind with a rigid platform.

An upper surface 2 of said extricator, i.e. the surface destined to support traumatised persons, presents a plurality of longitudinal ribs 3.

The aforementioned upper surface 2 presents, in correspondence with the area supporting the nape of the trauma victim, a recess 4 provided with two surfaces 5 mutually parallel according to the longitudinal axis of the extricator 1 and provided with inclination towards the interior of the extricator itself.

Two niches 6 and 6a are obtained, in the thickness of the extricator 1, on the lower surface 7 thereof and are destined to house belts 16 and 16a able to hold a trauma victim on the extricator.

The niches are positioned in correspondence with the points of the extricator 1 destined to support the occipital area and the torso of a trauma victim. The niches differ in shape, in particular the niche 6a is elongated and corresponds the area of the upper surface 2 where the sacral part of the trauma victim is set down, whilst the niche 6 has circular shape.

Two lids 8 and 8a correspond to the peripheral shape of the respective niches 6 and 6a. Both lids 8 and 8a are provided with tabs 9; said tabs are shaped in such a way as to adapt to corresponding slits 10 present, at the level of internal edges 11, on the peripheral edge of both niches 6 and 6a.

In the peripheral thickness of the edges of the body of the extricator 1 is obtained a plurality of openings 12; said openings are positioned symmetrically relative to the two longitudinal outer edges of the extricator itself and substantially in correspondence with the niches 6 and 6a.

The openings have a width that is slightly greater than the section dimension of the holding belts.

Two recesses 13 are obtained at an extremity of the extricator 1 and are obtained on the lower surface 7 thereof The edge of the upper surface 2, in correspondence with the recesses 13, presents a taper 14 of the thickness.

A handle (not illustrated) is disposed to extend from a surface 15 on the end of the extricator 1 opposite to the one containing the two recesses 13.

The operation of the extricator of the present invention shall now be described following the references indicated in the figures.

After aligning the patient's torso respecting its neutral position both on the sagittal and on the frontal plane, the extricator 1 is inserted behind the trauma victim's back exploiting, for that purpose, the taper 14 of the thickness of the extricator itself.

The presence of the longitudinal ribs 3 reduces the friction surface with the body of the trauma victim, favouring the insertion of the extricator 1.

The traumatised person is then embraced and the holding belts are extracted from the extricator 1 making them pass through the openings 12.

In performing this operation, care will be taken to start with the belts destined to the immobilisation of the shoulders of the traumatised person, then to continue with the belts relating to the pelvis, abdominal, and thigh areas.

Since only the extremities of the aforementioned belts project from the openings 12, it is sufficient to grip these extremities and pull: in this way the belts can easily be extracted from the respective niches 6 and 6a.

The fastening of the appropriate buckles (not illustrated) which are present on all such holding belts completes the operation of the immobilizing of the body of the traumatized person to the extricator 1.

At this point, after measuring the distance between the patient's nape and the plane of the extricator 1, an appropriate pillow is modelled and inserted into the recess 4 where the two surfaces 5, slightly inclined towards the interior of the extricator 1, guarantee that the aforementioned pillow is securely maintained in position; thereupon, the belts for holding the traumatised person's forehead and chin are extracted from the related openings 12. After completing these operations, the rescuers can move the traumatised person, now securely immobilised to the extricator 1, thanks to the presence of the handle 15 and of the recesses 13 for the insertion of the hands.

The description has specifically referred to the presence of two niches 6 and 6a, but it is evident that, conveniently, a single niche or even more than two niches may be provided. The description has specifically referred to the presence of niches and recesses of various kinds and positioning, so it is evident that the extricator of the present invention is preferably made using synthetic materials, in particular obtained by moulding or thermoforming, for instance high-density polyethylene, possibly reinforced with structural strengthening charges.

A second embodiment of the extricator of the present invention provides for the installation of automatic furling devices inside the niches 6 containing the holding belts. Upon freeing the traumatised person from said belts, the belts automatically retract inside the respective niches after the disengagement of the various buckles present on the belts themselves.

In an additional embodiment the extricator 1 is inserted inside the structure of the backrest of a racing car seat; the shape and the positioning of the extricator are able to ensure, in this embodiment too, the rapid extraction of the holding belts in spite of the exiguity and the particular shape of the available space.

This additional embodiment, when rescuing the traumatised driver, provides the capability of not opposing any hindrance to the releasing of the normal safety belts that hold the driver to the seat.

After performing this operation, rescuers extract the holding belts from the extricator, immobilising the driver therewith: thereupon, the driver him/herself can be extracted from the cockpit of the car, always maintained secured to the extricator, thereby avoiding any danger of stresses and bends to the entire spinal development.

The extricator of the present invention has the advantage of containing within its thickness all the holding belts destined to the immobilisation of traumatised persons, avoiding any danger or hindrance deriving from their dangling, and of being able immediately to use said belts simply by extracting them from the niches that contain them.

What is claimed is:

1. Shell extricator (1) of the type comprising an elongate rigid platform, characterized in that one or more niches (6) and (6a), destined to the containment of holding belts (16) and (16a), are formed in one side of said extricator; each said niche presenting the open side thereof on a lower surface (7) of the extricator (1) opposite to an upper surface (2) thereof destined to support thereon a traumatized person, the niches (6) and (6a) are positioned in correspondence with the areas of the extricator (1) destined to support respectively the occipital area and the torso of a traumatized person; the niches (6) and (6a) are provided with lids (8) and (8a); both lids (8) and (8a) are provided with tabs (9); and said tabs have a shape corresponding to that of slits (10) obtained on internal peripheral edges (11) of the niches (6) and (6a) and are able correctly to positioned the aforementioned lids.

2. An extricator (1) as claimed in claim 1, characterized in that in its peripheral thickness are formed openings (12); said openings are positioned symmetrically relative to the two longitudinal external edges of the extricator and are suitable for extracting the holding belts contained in the niches (6) and (6a); and the openings (12) present a width that is slightly greater than the section size of the aforementioned holding belts.

3. An extricator (1) as claimed in claim 1, characterized in that said upper surface (2), in the area designed to support the person's occipital area, presents a recess (4); two surfaces (5) of said recess, mutually opposite, have an inclination towards the interior of the extricator itself, and said recess is suitable for the positioning therein of a pillow.

4. An extricator (1) as claimed in claim 1, characterised in that inside one or more niches (6, 6*a*) are positioned devices for automatically furling the holding belts; said furling devices being suitable for automatically furling said holding belts and their positioning is such as to allow the closure of the respective containment niche (6, 6*a*) with the related lid (8, 8*a*).

\* \* \* \* \*